United States Patent [19]

Barrington

[11] Patent Number: 5,306,248
[45] Date of Patent: Apr. 26, 1994

[54] SELECTIVELY CONTROLLABLE INFLATION-DEFLATION DEVICE ADAPTED FOR USE IN ANGIOPLASTY PROCEDURES

[75] Inventor: James E. Barrington, Lexington, Mass.

[73] Assignee: C. R. Bard, Inc., Murray Hill, N.J.

[21] Appl. No.: 864,735

[22] Filed: Apr. 7, 1992

[51] Int. Cl.⁵ .................... A61M 29/00; A61M 5/00
[52] U.S. Cl. ...................... 604/97; 604/211; 604/99
[58] Field of Search ................ 604/96-101, 604/208-210, 118, 121, 228

[56] References Cited

U.S. PATENT DOCUMENTS

| | | |
|---|---|---|
| 2,475,939 | 7/1949 | Applezweig . |
| 4,153,056 | 5/1979 | Silver et al. . |
| 4,189,065 | 2/1980 | Herold . |
| 4,205,683 | 6/1980 | O'Neill . |
| 4,245,639 | 1/1981 | La Rosa . |
| 4,312,343 | 1/1982 | Leveen et al. . |
| 4,332,254 | 6/1982 | Lundquist . |
| 4,370,982 | 2/1983 | Reilly . |
| 4,439,185 | 3/1984 | Lundquist . |
| 4,457,712 | 7/1984 | Dragan . |
| 4,476,866 | 10/1984 | Chin . |
| 4,498,904 | 2/1985 | Turner et al. . |
| 4,560,352 | 12/1985 | Neumeister et al. . |
| 4,583,917 | 4/1986 | Shah . |
| 4,583,974 | 4/1986 | Kokernak . |
| 4,592,745 | 6/1986 | Rex et al. . |
| 4,651,738 | 3/1987 | Demer et al. . |
| 4,654,027 | 3/1987 | Dragan et al. . |
| 4,659,327 | 4/1987 | Bennett et al. . |
| 4,710,179 | 12/1987 | Haber et al. . |
| 4,723,938 | 2/1988 | Goodin et al. . |
| 4,743,230 | 5/1988 | Nordquest . |
| 4,758,223 | 7/1988 | Rydell . |
| 4,779,770 | 10/1988 | Herold . |
| 4,795,431 | 1/1989 | Walling . |
| 4,799,479 | 1/1989 | Spears . |
| 4,810,249 | 3/1989 | Haber et al. . |
| 4,820,287 | 4/1989 | Leonard . |
| 4,832,692 | 5/1989 | Box et al. . |
| 4,852,768 | 8/1989 | Bartsch . |
| 4,865,591 | 9/1989 | Sams . |
| 4,919,121 | 4/1990 | Rydell et al. . |
| 4,929,238 | 5/1990 | Baum . |
| 4,940,459 | 7/1990 | Noce . |
| 4,944,726 | 7/1990 | Hilal et al. . |
| 4,959,056 | 9/1990 | Dombrowski et al. . |
| 4,973,318 | 11/1990 | Holm et al. . |
| 4,976,725 | 12/1990 | Chin et al. . |
| 5,019,041 | 5/1991 | Robinson et al. . |
| 5,019,075 | 5/1991 | Spears et al. . |
| 5,047,015 | 9/1991 | Foote et al. . |
| 5,057,078 | 10/1991 | Foote et al. . |
| 5,084,017 | 1/1992 | Maffetone . |
| 5,084,060 | 1/1992 | Freund et al. ................ 606/192 |
| 5,147,300 | 9/1992 | Robinson et al. ............. 604/97 |
| 5,168,757 | 12/1992 | Rabenau et al. ............. 73/714 |
| 5,213,115 | 5/1993 | Zytkovicz et al. ........... 128/898 |

FOREIGN PATENT DOCUMENTS

WO90/11101  10/1990  PCT Int'l Appl. .
WO92/06735   4/1992  PCT Int'l Appl. .

Primary Examiner—John D. Yasko
Assistant Examiner—Adam J. Cermak
Attorney, Agent, or Firm—Morgan & Finnegan

[57] ABSTRACT

A selectively controllable inflation-deflation device for use with a balloon catheter during angioplasty procedures is disclosed. The device is constructed so that the piston shaft can be 1) locked and then rotatably and incrementally moved within the syringe cylinder to enable controlled pressurization, or 2) unlocked and moved within the cylinder to enable fluid purging of the cylinder and retraction of the piston shaft to a vacuum position. The device has a cylinder with proximal and distal ends and a fluid conduit adapted for communication with a balloon. A piston shaft is received within the proximal end of the cylinder. The piston shaft includes a piston mounted on the distal end of the shaft and the shaft is movable in one direction during inflation and in a second direction during deflation of the balloon. Screw threads are positioned on at least a portion of the piston shaft. A cam mechanism in the preferred form of a flexible arm and half nut member is mounted within the cylinder. A cam actuation mechanism in the preferred form of a collar is rotatably mounted on the cylinder and includes an extension that contacts a cam surface on the flexible arm and compresses the support arm to engage and disengage the half nut member with the threaded piston shaft.

7 Claims, 4 Drawing Sheets

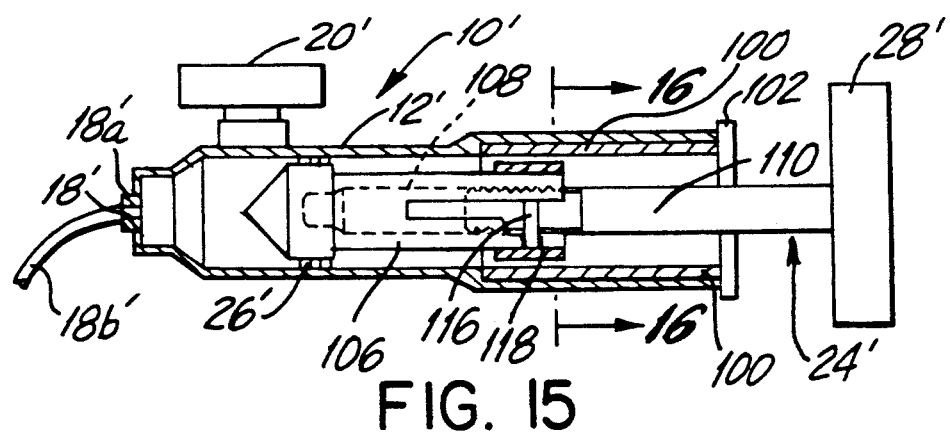
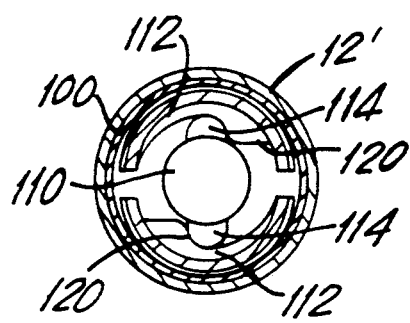
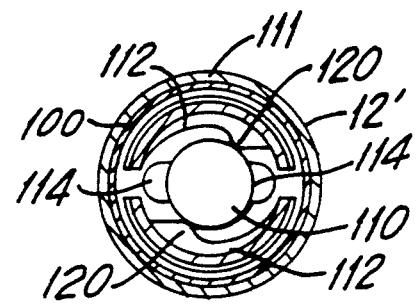
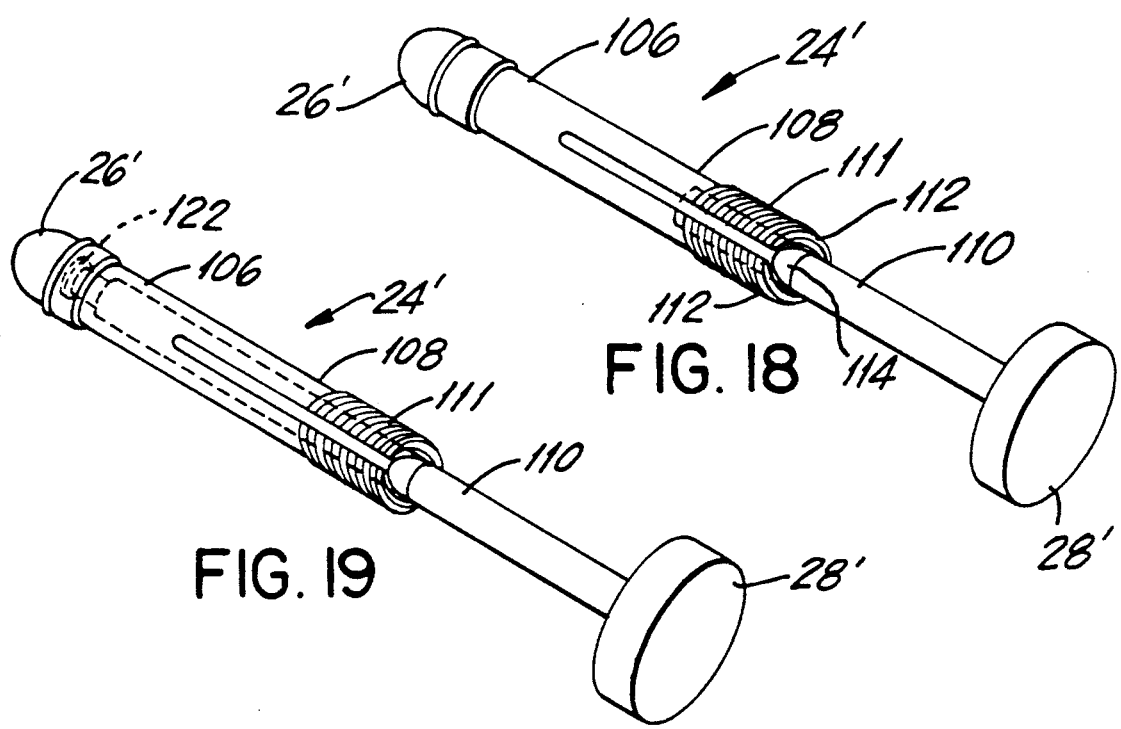

SELECTIVELY CONTROLLABLE INFLATION-DEFLATION DEVICE ADAPTED FOR USE IN ANGIOPLASTY PROCEDURES

FIELD OF THE INVENTION

This invention relates to a selectively controllable inflation-deflation device adapted for use in angioplasty procedures in which the piston shaft may be 1) locked and then rotatably and incrementally moved within the cylinder to enable controlled pressurization and 2) unlocked and moved or controllably moved within the cylinder to enable fluid purging of the cylinder and retraction of the piston shaft to a vacuum position.

BACKGROUND OF THE INVENTION

Inflation devices are commonly used by the medical profession in different applications, such as angiography and angioplasty procedures. Many of the inflation devices are simple in design, and mass produced from a plastic material. These basic inflation devices include a cylinder having a proximal end opening, a fluid conduit at the distal end which is adapted to be connected to a balloon, and a shaft and piston inserted within the proximal end of the cylinder for forcing fluid out of the fluid conduit when the piston shaft is extended into the cylinder.

Typically, simple syringes used as inflation devices are not designed to precisely control the amount of fluid discharged to the balloon. As a result, the devices are inadequate for many angioplasty procedures in which the pressure within the balloon must be precisely controlled. Angioplasty procedures require an inflation device that will accurately pressurize the balloon. Additionally, it is advantageous for an inflation device to allow the balloon to be selectively deflated during the procedure.

Various proposed inflation devices used in angioplasty and similar procedures provide for selective and controlled inflation and deflation of the balloon. For example, U.S. Pat. No. 4,583,974 to Kokernak discloses an inflation device for use in angioplasty in which a threaded half nut latch is pivotally attached to the cylinder. The shaft is threaded and the latch is manually moved between a disengaged position in which the shaft is free to move axially within the cylinder and an engaged position in which the half nut extends through a slot opening in the barrel to engage the threaded shaft to lock the shaft in position. In this locked position, the shaft is rotated to move the shaft within the cylinder.

U.S. Pat. No. 5,057,078 to Foote et al. discloses another inflation device in which a hand-held trigger is secured to the device handle to actuate sliding channels and a spring to force a threaded rack out of engagement with threads positioned on the interior surface of the cylinder. When the threads are engaged, the handle can be turned and the piston shaft may be incrementally moved within the cylinder to enable controlled pressurization. When the piston threads are not engaged, the piston shaft is unlocked and free to move axially within the cylinder.

Although these proposals provide an inflation device in which the piston shaft can be locked or unlocked for either controlled, incremental movement or free, axial movement within the cylinder, the proposed designs do not offer a mechanism for controlling locking and unlocking of the piston shaft which takes advantage of the cylindrical design of the inflation device. The cylindrical configuration of the cylinder and piston shaft can accommodate designs in which simple, rotatably movable components such as cams, cam followers, and semicircular shaped half nuts can be mounted within the cylinder and actuated by means external to the cylinder, such as a collar or the piston shaft itself. These mechanisms can in turn reliably lock and unlock threaded locking assemblies. Many locking mechanisms used with cylindrically configured inflation devices typically use racks or pivoted assemblies which are more complex, expensive, ergonomically inefficient, or difficult to use than the more desired rotatably movable components such as cams, cam followers, and half nuts.

OBJECTS OF THE INVENTION

It is therefore an object of the present invention to provide a selectively controllable inflation-deflation device for use with a balloon during angioplasty procedures in which rotatably movable components are mounted within the cylinder of the device and actuated by an external, easily manipulatable member for selectively locking and unlocking the piston shaft to allow controlled, incremental movement or free, axial movement of the piston shaft within the cylinder.

Another object of the present invention is to provide a selectively controllable inflation-deflation device for use with a balloon during angioplasty procedures in which a cam system selectively moves a threaded half nut in and out of engagement with a threaded piston shaft for providing controlled, incremental movement or free, axial movement of the piston shaft within the cylinder.

A further object of the present invention is to provide a selectively controllable inflation-deflation device for use with a balloon during angioplasty procedures in which rotative movement of the piston shaft controls locking and unlocking of the piston shaft within the cylinder for providing controlled, incremental movement or free, axial movement of the piston shaft within the cylinder.

A further object of the present invention is to provide a selectively controllable inflation-deflation device for use with a balloon during angioplasty procedures in which rotative movement of a component such as a collar engages and disengages a half nut with a threaded piston shaft for providing controlled, incremental movement or free, axial movement of the piston shaft within the cylinder.

Additional objects and advantages of the invention will be set forth in the description which follows and, in part, will be obvious from the description and advantages being realized and attained by means of the instrumentation, facts, apparatus, systems, steps and procedures particularly pointed out in the specification.

BRIEF DESCRIPTION OF THE INVENTION

In accordance with the present invention, a selectively controllable inflation-deflation device for use with a balloon catheter during angioplasty procedures is provided in which the piston shaft may be selectively locked and unlocked so that the shaft being either 1) locked and then rotatably and incrementally moved within the cylinder to enable controlled pressurization, or 2) unlocked and moved within the cylinder to enable fluid purging of the cylinder and retraction of the piston shaft to a vacuum position.

The inflation-deflation device of the invention includes a cylinder having proximal and distal ends, and a fluid conduit adapted for communication with a balloon. A piston shaft is received into the proximal end of the cylinder, and includes a piston mounted on the distal end of the shaft. The piston is movable in one direction during inflation and in a second direction during deflation of the balloon.

Threads are positioned on at least a portion of the piston shaft. Cam means is mounted within the cylinder and includes means for selectively engaging the threads on the shaft. Cam actuation means rotatably engages the cam means for selectively engaging and disengaging the cam means with the threaded piston shaft thereby allowing selected locking and unlocking of the piston shaft so that the piston shaft can be either 1) locked and then rotatably and incrementally moved within the cylinder, or 2) unlocked and moved within the cylinder to enable fluid purging of the cylinder and retraction of the shaft to a vacuum position where it may be relocked.

In a preferred embodiment, the cam means includes a flexible support arm mounted within the cylinder. The support arm includes an arcuate surface defining a cam surface. A threaded half nut member is supported by the support arm and positioned adjacent to the threaded piston shaft.

A collar is rotatably mounted on the outer, proximal surface of the cylinder. The collar has an extension extending into the cylinder, forming a cam follower that engages the cam surface of the flexible support arm. The cam surface is configured so that when the collar is turned, the cam follower moves on the cam surface to either compress the flexible arm member and engage the half nut member with the shaft or disengage the half nut member from the shaft thereby allowing selected locking and unlocking of the shaft. A stop is provided on the flexible support arm to prevent further rotation of the collar after the threaded half nut is engaged with the threaded piston shaft.

In the preferred embodiment, the flexible support arm comprises first and second segments extending approximately circumferentially about the shaft. Each segment includes corresponding cam surfaces, and a half nut member carried by the respective segments. The collar includes corresponding extensions acting as cam followers which engage the cam surfaces.

In another embodiment, the flexible support arm includes slots for receiving pins of the collar. The slots are configured to enable compression of the flexible support arm and movement of the half nut member into and out of engagement with the threaded shaft.

In still another embodiment, the cylinder includes internal threads. The piston shaft includes a distal shaft portion having a proximal, bifurcated end, and a proximal shaft portion rotatably received within the bifurcated end. The distal and proximal shaft portions are dimensioned in a clearance fit to permit rotation of the proximal shaft portion within the distal shaft portion. The bifurcated end includes threads thereon opposing to the cylinder threads. A cam surface is positioned on the interior surface of the bifurcated end of the piston shaft.

A cam follower is mounted on the surface of the proximal shaft portion within the bifurcated end. The cam follower is dimensioned to engage the cam surface when the proximal shaft portion is selectively turned so as to force the bifurcated end radially outward and force the threads into the threads positioned on the inner cylinder so that the shaft being either 1) locked and then rotatably and incrementally moved within the cylinder to enable controlled pressurization, or 2) unlocked and moved within the cylinder to enable fluid purging of the cylinder and retraction of the shaft to a vacuum position where it may be relocked.

The invention consists of the various parts, constructions, arrangements and improvements shown and described. The accompanying drawings which are incorporated in and constitute a part of the specification illustrate embodiments of the invention and together with the description serve to explain the principles of the invention.

DESCRIPTION OF THE DRAWINGS

The foregoing and other objects and advantages of the present invention will be appreciated more fully from the following description, with references to the accompanying drawings in which:

FIG. 15 is a schematic cross sectional view with partial cutaway of a fourth embodiment of the inflation device in which a proximal shaft portion is coaxially received into a distal shaft portion and wherein the piston shaft is locked by rotating the proximal shaft portion;

FIG. 16 is a schematic view of the fourth embodiment taken along line 16—16 of FIG. 15 and illustrating the cam followers of the proximal shaft portion engaging the cam surfaces on the distal shaft portion so the piston shaft is locked in position;

FIG. 17 is a schematic view of the fourth embodiment similar to the view of FIG. 16 and showing the cam followers disengaged from the cam surfaces so that the piston shaft is free to move axially within the cylinder;

FIG. 18 is an assembly view of the proximal and distal shaft portions in which the proximal shaft portion extends only partially into the distal shaft portion; and FIG. 19 is a view similar to FIG. 18 in which the proximal shaft portion extends fully through the distal shaft portion into the piston.

DETAILED DESCRIPTION OF THE INVENTION

Figure 1:
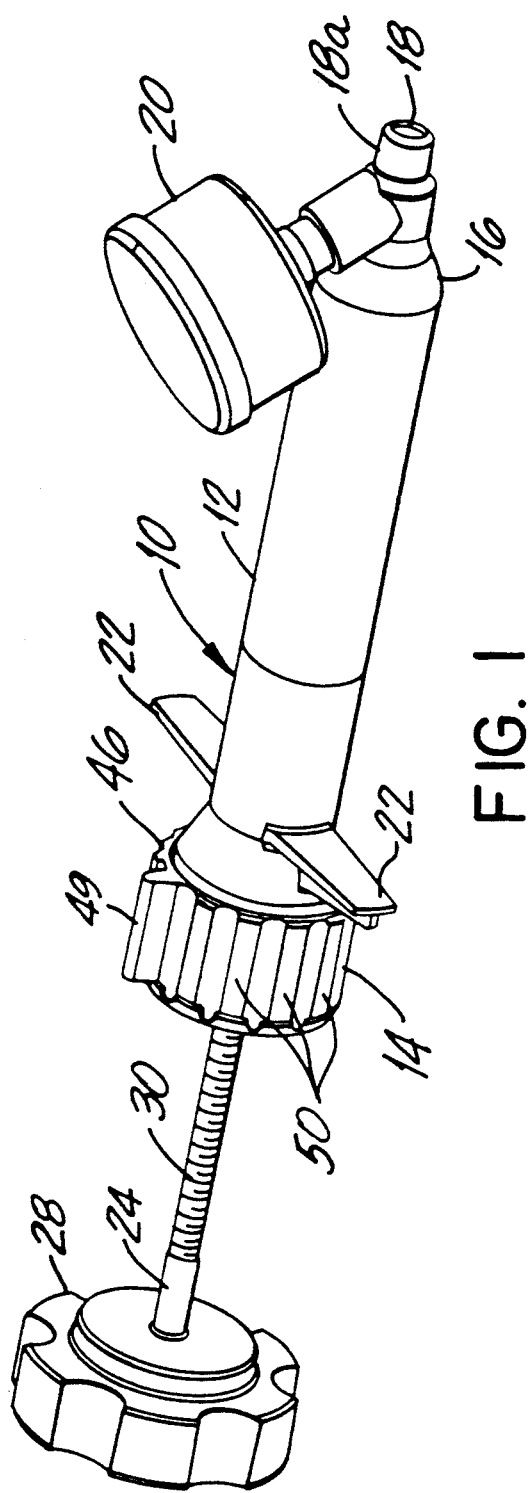
FIG. 1 is an isometric view of the inflation device in accordance with a first embodiment of the present invention.

Referring now to FIG. 1, there is illustrated at 10 a selectively controllable inflation-deflation device in accordance with a first preferred embodiment of the present invention, which is used with a balloon for angioplasty procedures and the like. The device 10 of the present invention provides a structure in which the piston shaft may be selectively locked and unlocked so that the piston shaft may be 1) locked and then rotatably and incrementally moved within the cylinder to enable controlled pressurization, or 2) unlocked and moved within the cylinder to enable fluid purging of the cylinder and retraction of the piston shaft to a vacuum position. As will be explained in detail below, the invention includes cam actuation means carried by the device which rotatably engages a cam assembly to force threads together.

In accordance with the first embodiment of the present invention, the device 10 includes a cylinder 12 having respective proximal and distal ends 14 and 16. The cylinder, also referred to as a barrel by those skilled in the art, is typically formed from injection molding of plastic material. The cylinder 12 includes a closed distal end 16 referred to as the box, having a fluid conduit 18 positioned at the distal end through which fluid may be conveyed to a PTCA balloon. The fluid conduit 18 is shaped to form a fitting 18a which is adapted to receive a catheter or other tube-like device 18b. A pressure gauge 20 is mounted at the distal end of the cylinder 12 and in communication with the internal area of the cylinder 12 to indicate the amount of pressure applied within the cylinder 12 and through the fluid conduit 18. Flanges 22 extend laterally outward from the cylinder 12 and are configured to be gripped by the fingers of one using the device 10.

Figure 2:
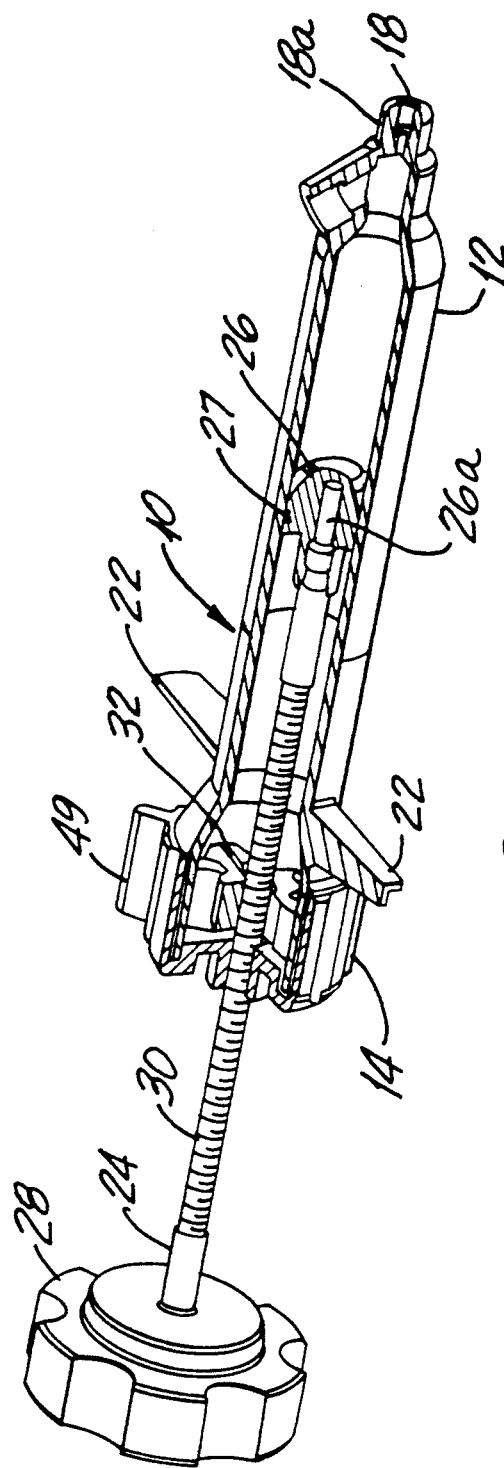
FIG. 2 is a sectioned, isometric view of the first embodiment of the inflation device of the present invention.
Figure 3:
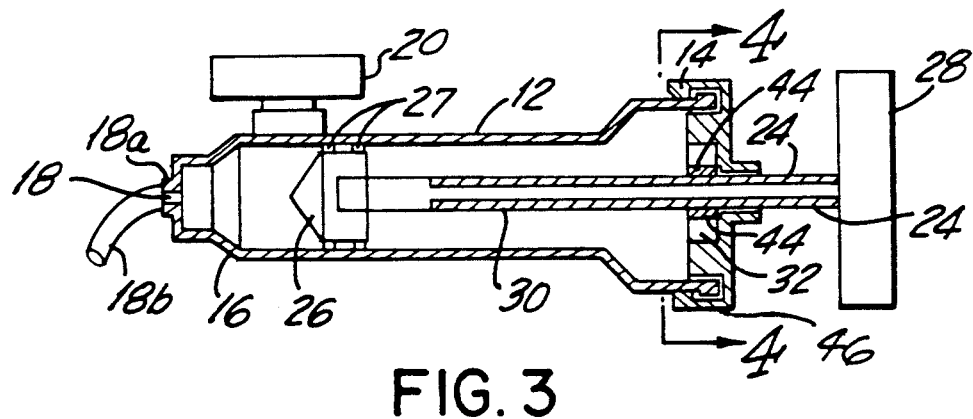
FIG. 3 is a schematic cross sectional view of the the first embodiment of the inflation device of the present invention.

As shown in greater detail in FIG. 2, a piston shaft 24 is received into the proximal end of the cylinder 12. The piston shaft 24 includes a piston 26 mounted on the distal end of the piston shaft. The piston 26 typically is rotatably mounted on the piston shaft 24 by a bearing assembly 26a which in the illustrated embodiment of FIG. 2 is formed by a thrust bearing surface at the lower end of the piston well and a lateral bearing surface at the sides. The piston 26 includes sealing rings 27 in FIG. 3; shown as one sealing ring in FIG. 2, which engages the interior and which is dimensioned to form a fluid tight seal with the internal walls of the cylinder 12 to prevent fluid from passing around the piston 26 as the piston shaft 24 is extended into the cylinder 12. A hand knob 28 is secured on the proximal end of the piston shaft 24 to facilitate grasping of the piston shaft 24 by the user. As shown in both FIGS. 1 and 2, the piston shaft 24 includes threads 30 positioned substantially along the length thereof.

Figure 4:
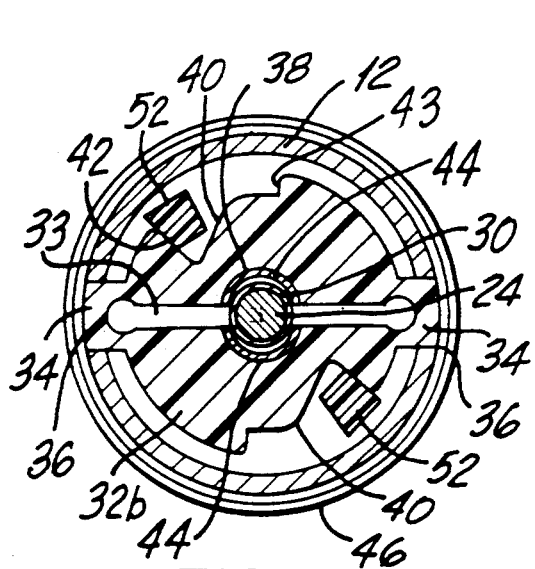
FIG. 4 is a schematic sectional view taken along line 4—4 of FIG. 3 and showing the half nut unengaged with the threaded shaft.
Figure 5:
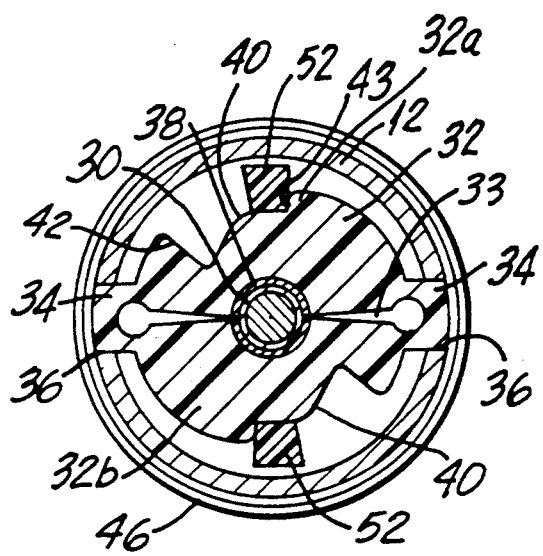
FIG. 5 is a schematic sectional view similar to FIG. 4 but showing the half nut engaged with the threaded shaft.

Referring now to FIGS. 4 and 5, a schematic representation of a flexible support arm 32 is shown mounted within the cylinder 12 at its proximal end 14. The flexible support arm 32 is formed of a semirigid plastic such as polyamide, sold under the tradename nylon, or acetal, sold under the tradenames Delrin or Celcon. Other materials commonly known to those skilled in the art also can be used. The arm 32 includes respective upper and lower integrally formed half segments 32a, 32b. The half segments 32a, 32b form a somewhat planar, circular configuration within the cylinder and include a longitudinal opening 33 in a medial portion. The two segments 32a, 32b are connected at their end portions to form at either end a rectangular configured mounting member 34. The rectangular configured mounting members 34 are received in opposing slots 36 formed in the wall surface of the cylinder. The slots 36 can extend partially or completely through the cylinder. Both upper and lower segments 32a, 32b also include semicircular cutouts 38 which form a circular opening through which the piston shaft 24 extends. Each segment 32a, 32b further includes an arcuate surface defining a cam surface 40.

Figure 6:
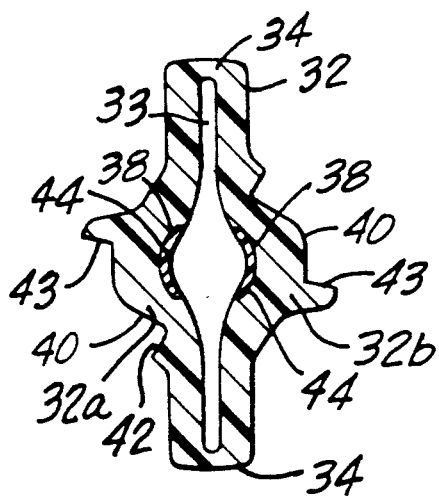
FIG. 6 is a sectional view of the flexible support arm on which the half nuts are carried.

FIG. 6 illustrates one proposed design showing an actual proposed configuration for a flexible arm member as compared to the schematic design used in the other figures.

Additionally, as shown in both embodiments, the cam surfaces are formed to respectively create stops 42, 43 at either end. Each semicircular cutout 38 also includes a threaded half nut member 44 carried by the support arm 32 therein. Each half nut may be secured by glue, integral molding on other common fastening techniques known to those skilled in the art. The half nut members 44 extend substantially circumferentially about the threaded piston shaft (FIGS. 4 and 5) and are positioned so that the threads are positioned adjacent to the threads of the piston shaft 30. The support arm segments are formed so that they are flexed and separated apart in a spring-like manner. When the cam surface is acted upon by a cam follower, as will be described later, the flexible arm 32 is compressed radially so that the half nuts 44 move radially into engagement with the threaded shaft. If two separate, nonintegrally formed segments are used, springs or other means may be used to flex and separate the arms from each other.

Figure 7:
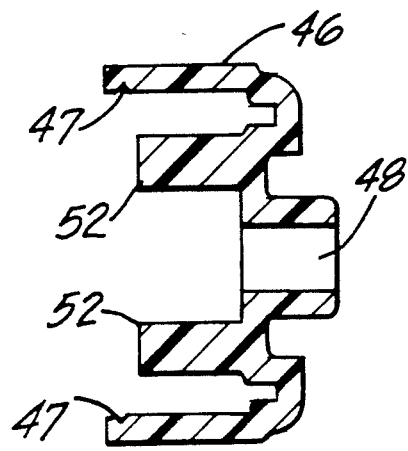
FIG. 7 is a sectional view of the collar in accordance with the first embodiment of the present invention.

As shown in FIGS. 1-7, a somewhat cup-shaped collar 46 is rotatably mounted on the proximal end 14 of the cylinder 12. The collar 46 is typically snap-fitted onto the proximal end of the cylinder 12 and includes a locking detent ring 47 for securing the collar 46 onto the proximal end. The collar 46 closes the proximal end of the cylinder, but includes an opening 48 through which the piston shaft 24 extends. A flange 49 extends laterally from the outer periphery of the collar. Preferably the periphery of the collar has formed grooves 50 to facilitate manual grasping and turning of the collar 46 by a user's engaging both the grooves and the flange. As shown in FIG. 7, the collar 46 includes upper and lower integrally formed extensions 52 extending into the proximal end of the cylinder 12. The extensions 52 form cam follower surfaces which engage the cam surface 40 and move over the cam surface (FIG. 4 and. FIG. 5) as the collar is rotated.

As shown in FIGS. 4 and 5, the cam surfaces 40 are configured so that when the collar is turned, the extensions 52 move over the cam surfaces 40 until they engage one of the stops 42, 43. In a first position shown in FIG. 4, the extensions 52 engage the stops 42. As shown in FIG. 4, in this position, the flexible support arm 32 is uncompressed and the half nut threads are unengaged with the threaded piston shaft 30. Looking in the direction of FIG. 4, the collar 46 is not free to further rotate in a clockwise direction because the extensions 52 engage the stops 42. Upon counterclockwise rotation of the collar 46, the extensions 52 move upward on the cam surfaces 40. The cam surfaces 40 are configured so that as the collar is rotated, the extensions 52 press against the flexible arm 32 and compress the segments 32A, 32B upon themselves to force the half nut 44 into engagement with the threaded shaft. In this position, the collar is prevented from further rotation because the extensions engage the stops 43.

In operation the device 10 is initially connected to a balloon catheter used in angioplasty procedures. The balloon catheter is connected via a tube or other connection means to the conduit fitting 18a positioned at the distal end of the cylinder, 12. The collar 46 is initially turned so that the cam followers 52 formed by the extension of the collar engage the stops 42 of the cam surfaces 40 formed on the support arms 32 as shown in FIG. 4.

In this operative position, the piston shaft 24 is unlocked, and the piston 26 may freely move within the cylinder 12. In this unlocked position the doctor or other user conducting the angioplasty procedure moves the piston shaft 24 axially forward within the cylinder to reach a somewhat pressurized position. The doctor then turns the collar 46 so that the cam followers 52 move over the cam surfaces 40 of the support arm 32 into a position engaging the stops, 43, shown in FIG. 5. In this position, the piston shaft 24 is locked. The doctor rotates the shaft 24 to incrementally move the piston shaft within the cylinder 12 allowing controlled pressurization of the balloon. After the requisite pressurization time has passed, the doctor may slowly relieve the pressure within the balloon by turning the piston shaft in a reverse direction to move the piston shaft 24 out of the cylinder 12. If an emergency arose, such as arterial damage resulting from excessive balloon pressure, and the balloon pressure had to be relieved quickly, the doctor can turn the collar 46, thereby unlocking the piston shaft 24 so that the doctor may pull the piston shaft 24 and quickly relieve the pressure.

Figure 8:
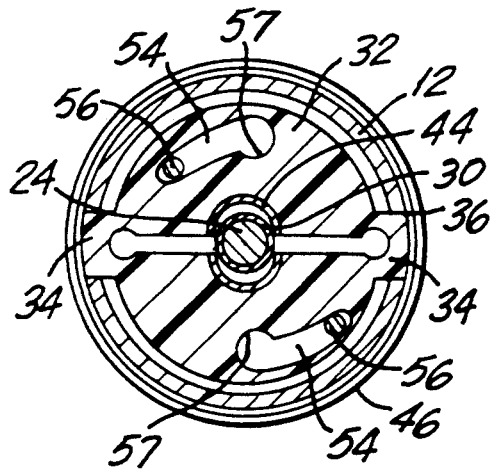
FIG. 8 is a schematic sectional view similar to FIG. 4 but showing a second embodiment of the device in which pins extend from the collar and are received through slots of the support arms.
Figure 9:
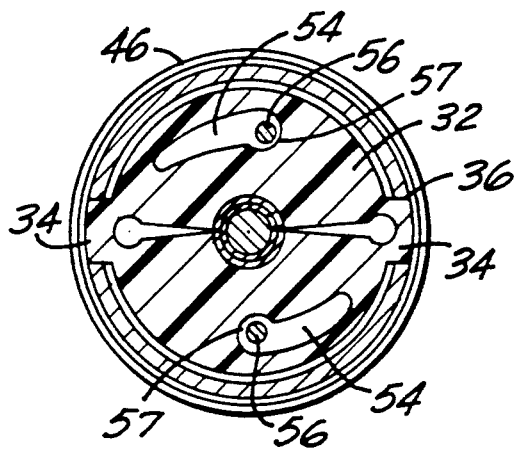
FIG. 9 is a schematic sectional view similar to FIG. 8 but showing the half nut engaged with the threaded shaft.
Figure 11:
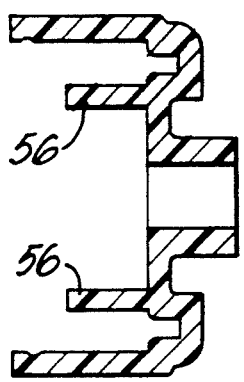
FIG. 11 is a sectional view of the collar used in the second embodiment of the present invention.

Referring now to FIGS. 8, 9 and 11, second embodiment of the device 10 is shown in which the arcuate configured cam surfaces on the flexible support arm 32 are replaced by upper and lower arcuate configured slots 54. The collar 46 includes integrally formed upper and lower pins 56 which are received into the slots 54. The slots 54 are configured so that as the collar is turned clockwise (FIG. 9), the flexible support arm 32 is compressed radially inward to force the half nuts into threaded engagement with the threaded shaft 30. The slots are dimensioned so that the collar 46 may be rotated only from the unengaged position shown in FIG. 8 to the engaged position shown in FIG. 9. Each slot also includes detents 57 for holding the pins 56 in place. In operation, the collar is moved as described in the operation of the first embodiment. The locking device 10 functions in a similar manner as described, except that the pins 56 acting as cam followers, move within the slots.

Figure 10:
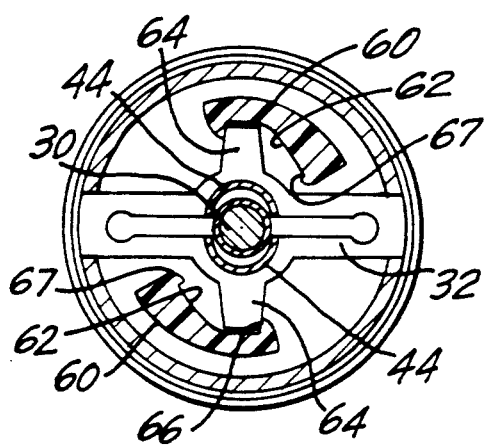
FIG. 10 is a schematic sectional view similar to FIG. 4, but illustrating a third embodiment in which the collar includes a cam surface for engaging a cam follower formed on the flexible arm member.
Figure 12:
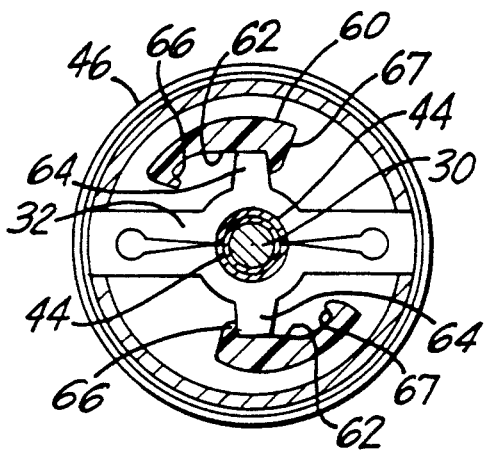
FIG. 12 is a schematic sectional view of the third embodiment similar to FIG. 10 but illustrating the half nut engaged with the threaded shaft.
Figure 14:
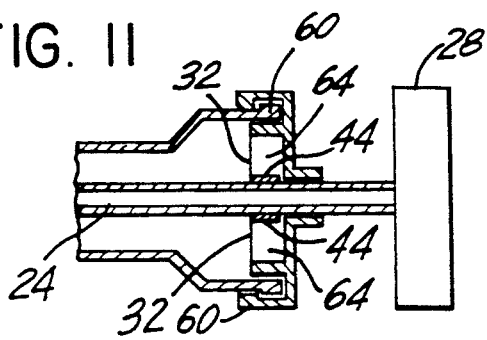
FIG. 14 is a schematic cross sectional view of the rear portion of a third embodiment of the inflation device.

FIGS. 10, 12 and 14 illustrate a third embodiment of the device 10 in which the collar 46 includes upper and lower cam protrusions 60 extending from the collar 46 into the cylinder 12. The protrusions include an arcuate surface defining upper and lower cam surfaces 62 which engage upper and lower cam followers 64 integrally formed on the flexible support arm 32. As shown in FIGS. 10 and 12, the flexible support arm 32 is configured somewhat differently from the previously described embodiments and do not include a slot or cam surface. In operation, as the collar is turned, the cam surfaces 62 engage the cam followers 64 and move from a first position (FIG. 10) in which the support arm is uncompressed and the half nut disengaged from the threaded shaft to a second position (FIG. 12) in which the support arm 32 is compressed radially toward the threaded shaft to force the half nut into engagement with the threaded shaft 30 (FIG. 12). The cam surfaces include end stops 66, 67 to prevent collar rotation beyond the points shown in FIGS. 10 and 12.

Figure 13:
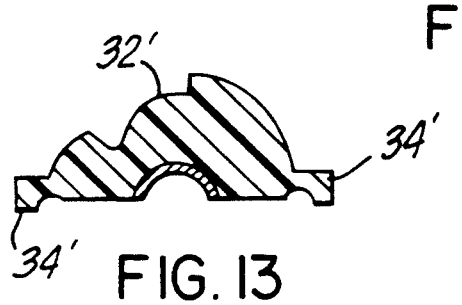
FIG. 13 is sectional view of another embodiment of the flexible support arm in which the arm is segmented into distinct, nonintegrally formed half segments.

FIG. 13 illustrates a flexible support arm embodiment designated by prime notation in which the two segments are not integrally formed together, but are formed as separate pieces. The segment includes end portions having rectangular configured supports 34' which are received into the slots 36 of the cylinder 12. As noted before, the two separate segments may include a spring or other means not shown positioned between the two members that flex and separate the members from each other so that in an uncompressed condition, the half nuts are unengaged with the threaded shaft.

Referring now to FIGS. 15-19, a fourth embodiment of the device 10 is illustrated in which the piston shaft is locked and unlocked by turning the piston shaft itself. The description of this embodiment will be described with similar reference numerals having prime notation and corresponding to the structure of the previous three embodiments. The new structural components differing from the structural components of the three previous embodiments will begin with the reference numeral 100.

As shown in FIG. 15, the cylinder 12' includes threads 100 positioned on the inside surface. A cap 102 is secured on the proximal end to close the cylinder 12' and to locate the shaft 24'. The cap 102 includes a combination piston shaft opening and shaft receiving bearing 104 through which the piston shaft extends into the cylinder 12'. The piston shaft 24' includes a distal shaft portion 106 having a proximal, bifurcated end 108. A proximal shaft portion 110 is rotatably received within the bifurcated end 108. The distal and proximal shaft portions 106, 110 are dimensioned in a clearance fit to allow rotation of the proximal shaft 110 relative to the distal shaft 106. An internal bearing assembly (not shown) can be used to rotatably support the distal and proximal shaft portions together.

As shown in FIGS. 18 and 19, threads 111 are positioned on the bifurcated shaft portion 108 and are positioned opposing the threads 100 positioned inside the cylinder. The inside surface of the bifurcated end 108 includes upper and lower cam surfaces 112. The proximal shaft portion 110 includes opposing cam followers 114 mounted on the proximal shaft portion within the bifurcated end 108. The followers 114 are dimensioned to engage the cam surface 112 when the proximal shaft portion 110 is selectively turned to force the bifurcated shaft portion radially outward so that the threads 111 are engaged with the threads 100 positioned on the inner surface of the cylinder.

The cam surfaces 112 include stops 120 (FIGS. 16 and 17) which prevent further turning of the proximal shaft portion 110 after the bifurcated end 108 is forced outwardly. Once the shaft is in this "locked" position with the distal shaft portion (FIG. 16), further turning of the proximal shaft portion 110 causes advancement of both shaft portions into the cylinder by means of the threaded assembly formed between the threads 100 or 111. When the proximal shaft portion 110 is turned counterclockwise (looking in the direction of FIGS. 16 and 17), the cam followers 114 are disengaged from the cam surface and the bifurcated end 108 is biased inwardly so that the threads are no longer engaged as shown in FIG. 17. Thus, the shaft 106, 110 can be moved axially within the cylinder. As shown in FIG. 15, an interlock means is provided for locking the proximal and distal shaft portions together. The interlock means of this embodiment includes an annular collar 116 secured to the proximal shaft portion. The collar 116 fits within a groove 118 positioned in the bifurcated end of the distal shaft portion. The two shaft portions can be axially moved together, but only rotatively moved together when the distal shaft portion is threadably coupled to the cylinder 12'.

FIGS. 18 and 19 illustrate two different embodiments of the shaft used in the illustrated embodiment in FIG. 15. In FIG. 18, the proximal shaft portion 110 extends only partially into the distal shaft portion 106 and terminates within the bifurcated end. The piston 26' is mounted at the end of the distal shaft portion 106 by means of a bearing assembly 122 shown in FIG. 19 by hidden lines. In FIG. 19, the proximal shaft portion 110 extends throughout the axial length of the distal shaft portion 106. The piston 26' is connected to the end of the proximal shaft portion 110 by means of a bearing assembly (FIG. 19). The bearing assembly provides free rotation of the piston 26' relative to the distal and proximal shaft portions 106, 110.

In operation, the device 10' in accordance with this fourth embodiment is initially connected to a balloon catheter used in angioplasty procedures. As with the other embodiments, the balloon catheter is connected via a tube or other connection means to the conduit fitting 18a positioned at the distal end of the cylinder 12'. The proximal shaft portion 110 is initially pressed in the forward direction. The interconnection formed between the annular collar 116 on the proximal shaft portion 110 and the groove 118 in the distal shaft portion 106 permits free rotation of the proximal shaft portion 110 within the distal shaft portion 106, while allowing axial movement of the two shaft portions 106, 110 together.

As the two shaft portions 106, 110 are moved axially forward, the balloon is pressurized. When the doctor turns the proximal shaft portion 110, the follower 114 engages the cam surface, locks the two together when it engages the stop 120, and forces the threads 111 on the bifurcated end of distal shaft, 106, into the threads 100 positioned on the inside surface of the cylinder 12'. As the proximal shaft portion 110 is turned more, the locking interengagement of the threads causes the shaft portions 106, 110 to advance incrementally within the cylinder. When the proximal shaft portion 110 is turned the other direction, the follower 114 disengages from the cam surface and the arms of the bifurcated end retract so that the threads rapidly disengage with each other. As a result, the balloon is rapidly deflated.

The embodiments of the present invention offer several advantages over other proposed inflation devices previously described. The device 10 of the present invention includes rotatably movable components which are mounted within the cylinder and actuated by an external, easily manipulatable component such as a collar or the shaft itself. The half nuts can be readily moved into and out of engagement with the threaded piston shaft. The embodiment of FIG. 15 provides for a device 10 in which only one manual activity is required to lock the piston shaft and move the shaft within the cylinder to enable controlled pressurization. As shown and illustrated in FIGS. 16 and 17, the proximal shaft portion is initially rotated to move the followers 114 into position as shown in FIG. 16. Upon further rotation, while the threads 100, 111 are engaged, the piston shaft is incrementally moved forward within the cylinder as the shaft is rotated.

It should be understood, that the foregoing description of the invention is intended merely to be illustrative thereof, and that other embodiments, modifications and equivalents may be apparent to those skilled in the art without departing from its spirit.

That which is claimed is:

1. A selectively controllable inflation-deflation device for use with a balloon catheter during angioplasty procedures comprising:
   (a) a cylinder having proximal and distal ends and a fluid conduit adapted for communication with a balloon;
   (b) a piston shaft received within the proximal end of said cylinder, said piston shaft including a piston mounted on the distal end of said shaft, said piston being movable in one direction during inflation and in a second direction during deflation of the balloon;
   (c) screw threads positioned on at least a portion of said piston shaft;
   (d) a flexible support arm said flexible support arm mounted within said cylinder, said flexible support arm comprising cam means and including means for selectively engaging said threads on said piston shaft; and
   (e) a collar mounted on an outer surface of said proximal end of said cylinder and comprising cam actuation means for rotatably engaging said cam means for selectively engaging and disengaging said thread on said piston shaft thereby allowing selective locking and unlocking of said piston shaft so that said piston shaft can be either 1) locked and then rotatably and incrementally moved within said cylinder to enable controlled pressurization of depressurization or 2) unlocked and moved within the cylinder to enable fluid purging of the cylinder and retraction of said piston shaft to a vacuum position where it may be selectively relocked to maintain said vacuum.

2. A device as defined in claim 1 having means for permitting unopposed deflation when said piston shaft is in the unlocked position.

3. A device as defined in claim 1 having means for permitting controlled deflation when said piston shaft is in the locked position.

4. A device as defined in claim 1 wherein said flexible support arm comprises a threaded half nut member mounted within said cylinder and supported by said flexible arm which engages said shaft upon selected actuation of said cam means.

5. A device as defined in claim 4 wherein said support arm includes an arcuate surface defining a cam surface engaged by said cam actuation means, where said cam surface is configured to affect flexure of said support arm and corresponding engagement of said half nut with said piston shaft upon actuation by said cam actuation means.

6. A device according to claim 5 wherein said flexible support arm comprises two half segments extending substantially circumferentially about a portion of said shaft, and including means for separating said segments away from said shaft when said support arm segments are not flexed by said cam actuation means.

7. A device as defined in claim 1 said flexible support arm including means for limiting rotation of said cam actuation means when said means for selectively engaging said threads on said piston shaft is either threadably engaged to said threaded piston shaft means or threadably disengaged from said threaded piston shaft means.

* * * * *